United States Patent
Wilke et al.

(10) Patent No.: US 10,267,760 B2
(45) Date of Patent: Apr. 23, 2019

(54) SENSOR ARRANGEMENT AND METHOD FOR DETERMINING ORTHOPHOSPHATE CONTENT OF A LIQUID

(71) Applicant: Endress + Hauser Conducta Gesellschaft für Mess- und Regeltechnik mbH + Co. KG, Gerlingen (DE)

(72) Inventors: Stefan Wilke, Halle (DE); Thomas Wilhelm, Chemnitz (DE)

(73) Assignee: Endress+Hauser Conducta GmbH+Co. KG, Gerlingen (DE)

( * ) Notice: Subject to any disclaimer, the term of this patent is extended or adjusted under 35 U.S.C. 154(b) by 805 days.

(21) Appl. No.: 14/571,450

(22) Filed: Dec. 16, 2014

(65) Prior Publication Data
US 2015/0177182 A1   Jun. 25, 2015

(30) Foreign Application Priority Data
Dec. 19, 2013  (DE) .................. 10 2013 114 481

(51) Int. Cl.
*G01N 27/333*        (2006.01)
(52) U.S. Cl.
CPC ................ *G01N 27/333* (2013.01)
(58) Field of Classification Search
CPC ........ G01N 27/27; G01N 27/28; G01N 27/30; G01N 27/333; G01N 27/3335
See application file for complete search history.

(56) References Cited

U.S. PATENT DOCUMENTS

| | | |
|---|---|---|
| 5,180,481 A | 1/1993 | Carey |
| 8,124,418 B2 | 2/2012 | Haruyama |
| (Continued) | | |

FOREIGN PATENT DOCUMENTS

| | | |
|---|---|---|
| CN | 1098502 A | 2/1995 |
| DE | 102009051169 A1 | 5/2011 |
| (Continued) | | |

OTHER PUBLICATIONS

J.K. Tsagatakis, et al., "Multiorganyltin Compounds. Designing a Novel Phosphate-Selective Carrier", Chimica Acta, vol. 77 (1994), pp. 2191-2196.*

(Continued)

*Primary Examiner* — Maris R Kessel
(74) *Attorney, Agent, or Firm* — Christopher R. Powers; PatServe

(57) ABSTRACT

A method for determining orthophosphate content of a liquid, comprising: registering a first measurement signal (ISE1) of an ion selective dihydrogen phosphate sensor; registering a second measurement signal (ISE2) of an ion selective hydrogen phosphate sensor; and determining the orthophosphate content of the liquid based on the first (ISE1) and second (ISE2) measurement signals. The dihydrogen phosphate sensor can comprise an ion selective dihydrogen phosphate electrode and the hydrogen phosphate sensor an ion selective hydrogen phosphate electrode. In the step of determining the orthophosphate content of the liquid, a cross-sensitivity of the dihydrogen phosphate electrode to hydrogen phosphate present in the liquid and a cross-sensitivity of the hydrogen phosphate electrode to dihydrogen phosphate present in the liquid can be taken into consideration.

10 Claims, 4 Drawing Sheets

(56) References Cited

U.S. PATENT DOCUMENTS

| | | | |
|---|---|---|---|
| 2002/0043459 A1* | 4/2002 | Kobayashi | G01N 27/333 204/419 |
| 2003/0166736 A1* | 9/2003 | Kawai | G01N 27/3335 522/1 |

FOREIGN PATENT DOCUMENTS

| | | | | |
|---|---|---|---|---|
| EP | 1767931 A1 | | 3/2007 | |
| GB | 2503689 A | * | 1/2014 | G01N 27/4035 |
| GB | 2503689 A | | 1/2014 | |

OTHER PUBLICATIONS

D. Liu et al., "Polymeric Membrane Phosphate Sensitive Electrode Based on Binucle Organotin Compound", Analyt. Chim. Acta 338 (1997), pp. 209-214.*

C. M. Carey, et al., Cyclic Polyamine Ionophore for Use in a Dibasic Phosphate-Selective Electrode, Anal. Chem., vol. 66, pp. 3587-3591 (1994).*

H.J. Kim, et al., Evaluation of Phosphate Ion-Selective Membranes and Cobalt-Based Electrodes for Soil Nutrient Sensing, Transactions of the ASABE, vol. 50, Issue 2, pp. 415-425 (2007).*

R. De Marco, et al., Flow injection potentiometric determination of phosphate in waste waters and fertilizers using a cobalt wire ion-selective electrode, Analyst, vol. 123, pp. 1635-1640 (1998).*

M. Fibbioli, et al., Polymeric Membrane Electrodes for Monohydrogen Phosphate and Sulfate, Anal. Chem., vol. 72, pp. 156-160 (2000).*

K. Cammann, H. Galster, Das Arbeiten mit ioneriselektiven Elektroden (Working with Ion-Selective Electrodes), 3rd Edition, Chapters 3.2.1.1-3.2.1.2 and Chapter 3.2.2.4, pp. 63-65, 72-81, Springer Verlag (publisher), 1996.

* cited by examiner

SENSOR ARRANGEMENT AND METHOD FOR DETERMINING ORTHOPHOSPHATE CONTENT OF A LIQUID

TECHNICAL FIELD

The invention relates to a sensor arrangement and to a method for determining the orthophosphate content of a liquid.

BACKGROUND DISCUSSION

Determining the concentration of orthophosphate $PO_4^{3-}$ in process analysis, especially in the application domains of water and waste water, is of worldwide interest. This parameter plays an important role especially for monitoring bodies of water, for monitoring the maintaining of prescribed P discharge limit values in industrial and community clarification plants, and, in given cases, for the control of the phosphate elimination, respectively phosphate reclamation, performed in such clarification plants.

To this point in time, the determining of orthophosphate in these applications is frequently performed by means of laboratory analyses. As a rule, this permits no near in time determining of measured values. A providing of measured values in real time, such as is required for the automated control of processes, is likewise not possible by means of laboratory analyses.

To this point in time, known automatic analysis measuring devices for orthophosphate determination, especially on-line measuring devices, can, indeed, in principle, be applied for automated control. However, the measured value determination in these analytical measuring devices is based on wet chemical analytical methods. These require the application of chemical reagents, with which a liquid sample is treated, in order to bring about an, as a rule, photometrically detectable change of the properties of the liquid sample, e.g. a coloring or a color change, dependent on the orthophosphate content. These analytical devices deliver, indeed, very exact measurement results. However, they are relatively complicated in construction and require significant maintenance. Especially, reagents and, in given cases, wear parts need regularly to be replaced.

In situ sensors, such as optrodes or ion-selective electrodes, form for determining concentration of many ions a relatively cost effective and less maintenance demanding alternative, which virtually continuously provide measured values of ion concentrations without sample taking and without addition of reagents. An ion-selective electrode is a potentiometric sensor having a measuring half cell and a reference half-cell. The measuring half cell includes a measuring membrane, at which a potential arises dependent on the concentration of a certain kind of ion. Used as reference half-cell can be, for example, a reference electrode of second type, e.g. a silver/silver chloride, reference electrode, which provides a stable reference potential independent of the measured variable. The determining of ion concentration occurs based on the potential difference registered between the measuring half cell and the reference half-cell when in contact with a measured liquid. A number of examples of ion-selective electrodes are given, for example, in K. Cammann, H. Galster, Das Arbeiten mit ionenselektiven Elektroden (Working with Ion-Selective Electrodes), 3rd Edition, Springer Verlag (publisher), 1996.

SUMMARY OF THE INVENTION

An object of the invention includes a method and a sensor arrangement, which provide a cost effective and, in comparison to the known, wet chemical method based, analytical devices, less maintenance intensive alternative for determining orthophosphate content of a liquid.

This object is achieved according to the invention by a method.

The method of the invention for determining orthophosphate content of a liquid comprises:
registering a first measurement signal of an ion-selective dihydrogen phosphate sensor;
registering a second measurement signal of an ion-selective hydrogen phosphate sensor; and
determining the orthophosphate content of the liquid based on the first and second measurement signals.

The method of the invention is based on the recognition that in a large number of applications, in which the orthophosphate content of a liquid must be determined, the two ion types, dihydrogen phosphate and hydrogen phosphate, the latter of which is also referred to as monohydrogen phosphate, provide the essential contribution to orthophosphate content. Especially in the application domain of monitoring bodies of water or in the monitoring or controlling of phosphate elimination, or phosphate reclamation, processes in clarification plants, the pH-value of the liquid to be monitored, i.e. the body of water, respectively the waste water to be treated, lies, as a rule, in a range between 5 and 10, frequently even only between 7 and 8. In this pH range, orthophosphate is present almost exclusively as hydrogen phosphate $HPO_4^{2-}$ and/or as dihydrogen phosphate $H_2PO_4^-$. The pH-value of the liquid determines the ratio, with which these two ion types coexist. For determining orthophosphate content for the purpose of controlling a phosphate elimination process, respectively a phosphate reclamation process, as well as for monitoring a clarification plant outlet or a natural body of water, consequently, as a rule, an orthophosphate content ascertained with the method of the invention is sufficient. Preferably, the orthophosphate content of the sample is, consequently, ascertained exclusively based on the first and second measurement signals.

By applying an ion-selective dihydrogen phosphate sensor and an ion-selective hydrogen phosphate sensor for registering the first and second measurement signals, measured values can be ascertained in situ virtually continuously and provided to a control unit. The ion-selective dihydrogen phosphate sensor can comprise an ion-selective dihydrogen phosphate electrode, while the ion-selective hydrogen phosphate sensor can correspondingly comprise an ion-selective hydrogen phosphate electrode. Maintenance intensive, analytical devices are then no longer needed. Ion selective electrodes for dihydrogen phosphate, in the following also referred to as DHP, and for hydrogen phosphate, in the following also referred to as MHP, are known from the literature. For example, known from the article "Multiorganyltin Compounds. Designing a Novel Phosphate-Selective Carrier", J. K. Tsagatakis, N. A. Chaniotakis and K. Jurkschat. Helv. Chimica Acta, Vol. 77 (1994), Pgs. 2191-2196, is an ion selective DHP electrode and from the article "Polymeric Membrane Phosphate Sensitive Electrode Based on Binuclear Organotin Compound", D. Liu, W.-C. Chen, R.-H. Yang, G.-L. Shen and R.-Q. Yu. Analyt. Chim. Acta 338 (1997), Pgs. 209-214, an ion-selective MHP electrode.

Ion selective electrodes respond selectively, however, not specifically, to certain ions. Consequently, cross sensitivities to other ions can occur. Especially, the known ion-selective DHP electrodes also have a certain sensitivity to MHP, while the known MHP electrodes possess a cross-sensitivity to DHP. In an advantageous embodiment of the method, consequently, in the step of determining the orthophosphate content of the liquid, a cross-sensitivity of the dihydrogen phosphate electrode to hydrogen phosphate present in the liquid and a cross-sensitivity of the hydrogen phosphate electrode to dihydrogen phosphate present in the liquid are taken into consideration.

For determining the orthophosphate content of the liquid, in a first step, a dihydrogen phosphate concentration is ascertained from the first measurement signal and a hydrogen phosphate concentration from the second measurement signal. These concentrations are, in each case, somewhat too high, due to the mentioned cross sensitivities of the ion-selective electrodes. Advantageously, consequently, the dihydrogen phosphate concentration ascertained from the first measurement signal and the hydrogen phosphate concentration ascertained from the second measurement signal can be corrected by taking into consideration the cross-sensitivity of the dihydrogen phosphate electrode to the hydrogen phosphate present in the liquid to ascertain a corrected dihydrogen phosphate concentration and by taking into consideration the cross-sensitivity of the hydrogen phosphate electrode to the dihydrogen phosphate present in the liquid to ascertain a corrected hydrogen phosphate concentration.

In practice, a measurement signal dependent on the activity of the kind of ion to be determined is registered with the assistance of a potentiometric, ion-selective electrode. The measured values derived from the measurement signals are, thus, strictly interpreted, likewise ion activities. In dilute solutions, such as is the case for the liquids occurring in the already mentioned fields of application in process analytics and in water body monitoring, the ion activities are, as a rule, equal to the ion concentrations. The terms "concentration" and "activity" are, consequently, to be understood as synonymous for the application of the invention.

The ascertaining of the corrected dihydrogen phosphate concentration and/or the corrected hydrogen phosphate concentration can occur based on the Nikolsky-Eisenman equation.

Especially, the corrected dihydrogen phosphate concentration ($c_{DHP}$) and the corrected hydrogen phosphate concentration ($c_{MHP}$) can be ascertained from the concentrations ascertained based on the measurement signals with application of the selectivity coefficients ($k_1$, $k_2$) of the dihydrogen phosphate electrode (2) and the hydrogen phosphate electrode (3), especially based on the following system of equations:

$$c_1 = c_{DHP} + (k_1 c_{MHP})^{1/2}$$

and $$c_2 = c_{MHP} + (k_2 c_{DHP})^2,$$

wherein $c_1$ is the dihydrogen phosphate concentration ascertained from the first measurement signal, $c_2$ is the hydrogen phosphate concentration ascertained from the second measurement signal, $k_1$ is the selectivity coefficient of the dihydrogen phosphate electrode, and $k_2$ is the selectivity coefficient of the hydrogen phosphate electrode.

For example, the corrected dihydrogen phosphate concentration can be ascertained based on the equation ascertained from above system of equations $$c_{DHP} = \frac{c_1 - \sqrt{k_1(k_1 k_2^2 + 1)c_2 - k_1 k_2^2 c_1^2}}{k_1 k_2^2 + 1}$$

wherein $c_1$ is the dihydrogen phosphate concentration ascertained from the first measurement signal, $c_2$ is the hydrogen phosphate concentration ascertained from the second measurement signal, $k_1$ is the selectivity coefficient of the dihydrogen phosphate electrode, and $k_2$ is the selectivity coefficient of the hydrogen phosphate electrode. Based on the so ascertained, corrected dihydrogen phosphate concentration ($c_{DHP}$), a corrected hydrogen phosphate concentration ($c_{MHP}$) can be calculated, especially based on the equation $$c_{MHP} = c_2 - (k_2 c_{DHP})^2.$$

In another method variant, likewise based on the Nikolsky-Eisenman equation, respectively the above system of equations, first of all, the corrected hydrogen phosphate concentration can be ascertained based on the equation $$c_{MHP} = c_2 - k_2^2 \left( \frac{c_1 - \sqrt{k_1(k_1 k_2^2 + 1)c_2 - k_1 k_2^2 c_1^2}}{k_1 k_2^2 + 1} \right)^2$$

wherein $c_1$ is the dihydrogen phosphate concentration ascertained from the first measurement signal, $c_2$ is the hydrogen phosphate concentration ascertained from the second measurement signal, $k_1$ is the selectivity coefficient of the dihydrogen phosphate electrode, and $k_2$ is the selectivity coefficient of the hydrogen phosphate electrode. Based on the so ascertained, corrected hydrogen phosphate concentration ($c_{MHP}$), a corrected dihydrogen phosphate concentration ($c_{DHP}$) can be calculated, especially based on the equation $$c_{DHP} = c_1 - (k_1 c_{DHP})^{1/2}.$$

The orthophosphate concentration can then be determined by addition of the corrected dihydrogen phosphate concentration and the corrected hydrogen phosphate concentration.

The liquid can, such as already mentioned, be an aqueous liquid, especially a body of water or waste water treated in an industrial or a community clarification plant. Preferably, the liquid has a pH-value between 5 and 10.

A sensor arrangement suitable for determining orthophosphate content of a liquid according to the above described method includes:
- an ion-selective hydrogen phosphate sensor, an ion-selective dihydrogen phosphate sensor, and
- an electronic control unit, which is embodied to receive and to process further, especially to digitize, measurement signals produced by the ion-selective sensors and which includes a computing unit, which is embodied to execute a computer program serving for performing the above described method of the invention or one of the above described optional embodiments.

The ion-selective hydrogen phosphate sensor can comprise an ion-selective hydrogen phosphate electrode. The ion-selective dihydrogen phosphate sensor can comprise an ion-selective dihydrogen phosphate electrode.

The ion-selective electrodes can be accommodated in a shared housing. Advantageously, the two ion-selective electrodes use the same reference half-cell.

BRIEF DESCRIPTION OF THE DRAWINGS

The invention will now be explained in greater detail based on the examples of embodiments illustrated in the appended drawing, the figures of which show as follows.

DETAILED DISCUSSION IN CONJUNCTION WITH THE DRAWINGS

The molar concentration of orthophosphate is composed of the four sub-concentrations of phosphoric acid $H_3PO_4$, dihydrogen phosphate (DHP) $H_2PO_4^-$, hydrogen phosphate (MHP) $HPO_4^{2-}$ and phosphate $PO_4^{3-}$:

$$c_{orthophosphate} = c_{phosphoric\ acid} + c_{DHP} + c_{MHP} + c_{phosphate}.$$

Figure 1:
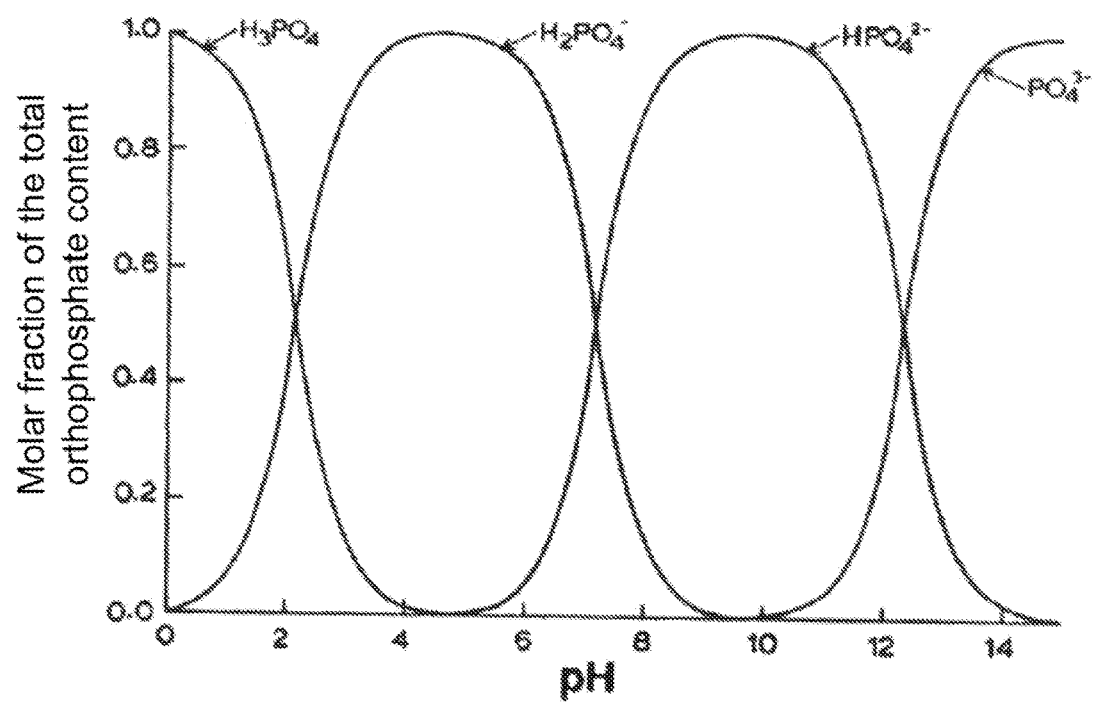
FIG. 1 is a schematic diagram of the molar fractions of various ion species present in orthophosphate solution as a function of the pH-value of the solution.

Based on the chart illustrated in FIG. 1, in which the molar fractions of the total-orthophosphate content of various ion types contributing to the orthophosphate content of a liquid are plotted versus the pH-value of the liquid, it can be seen that, in the pH-value range between 5 and 10, the concentrations of phosphoric acid and of phosphate are negligibly small. In these pH regions, in which also the pH-values of bodies of water and of waste water in clarification plants reside, the contribution of phosphoric acid and phosphate to the orthophosphate content lies, consequently, below the measurement error of ion selective electrodes or optodes and need, consequently, not be taken into consideration in the orthophosphate determination. The orthophosphate content of the liquid is composed, consequently, exclusively of the two concentrations of DHP and MHP.

When thus with a first sensor the DHP part and with a second sensor the MHP part of the orthophosphate content is measured, at least within the broad value range between pH 5 and pH 10 no pH-value compensation of the measurement results is required. Rather, over that entire pH-value range a determining of the DHP- and the MHP concentrations suffices, wherein the orthophosphate content is computed as the sum of the two concentrations.

Figure 2:
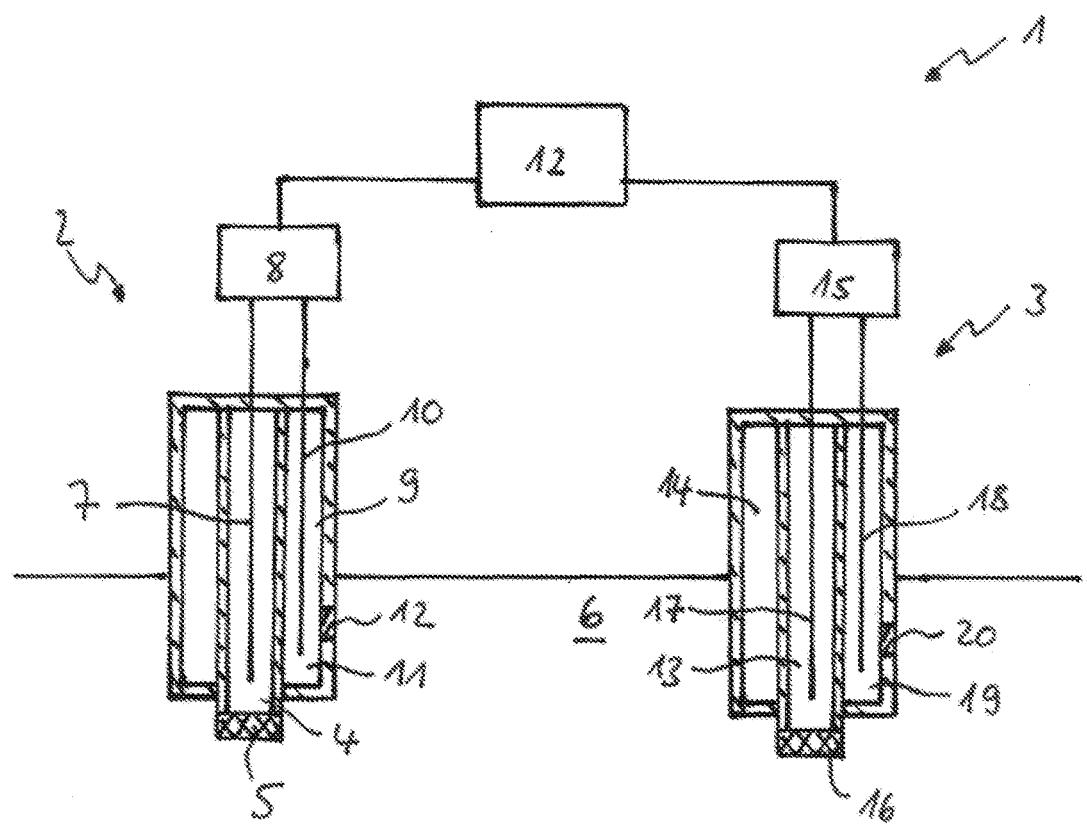
FIG. 2 is a schematic representation of a first sensor arrangement for determining orthophosphate content.

FIG. 2 shows a first example of a sensor arrangement 1 serving for determining orthophosphate content. Sensor arrangement 1 includes two ion-selective electrodes 2 and 3 embodied as single-rod, measuring chains. The first electrode 2 of the two ion-selective electrodes is embodied as a DHP selective electrode, while the second ion selective electrode 3 is embodied as an MHP selective electrode. The first ion selective electrode 2 includes a measuring half cell 4 with a DHP selective membrane 5, at which in contact with a liquid 6 a potential dependent on the MHP concentration in the liquid arises. The measuring half cell 4 includes, moreover, a potential sensing element 7 in electrical contact with the DHP selective membrane 5, in given cases, via an internal electrolyte, and electrically connected with a measurement circuit 8. The reference half-cell 9 of the first ion selective electrode 2 is embodied as a silver/silver chloride reference electrode and includes a reference element embodied as a chloridized silver wire, and extending into a reference electrolyte 11, e.g. a 3 M potassium chloride solution. The reference electrolyte 11 is in electrolytic contact with the liquid 6 via an electrochemical liquid junction 12, e.g. a diaphragm, arranged in the wall of the reference half-cell 9. Reference element 10 is likewise electrically conductively connected with the measurement circuit 8. Measurement circuit 8 is embodied to register a potential difference between the potential sensing element 7 and the reference element 10 and to output such, or a signal derived therefrom, as a measurement signal of the first ion selective electrode 2 to a superordinated control unit 12 connected with the measurement circuit 8.

The second ion selective electrode 3 likewise includes a measuring half cell 13 and a reference half-cell 14 as well as a measurement circuit 15. The measuring half cell 13 includes a MHP selective membrane 16, at which in contact with the liquid 6 a potential arises dependent on the MHP concentration in the liquid 6, and a potential sensing element 17, which is in electrical contact with the membrane 16, and which is embodied for sensing the potential arising at the membrane 16. Potential sensing element 17 is connected with the measurement circuit 15. The reference half-cell 14 includes a silver/silver-chloride electrode of equal construction to that of the reference half-cell 9 of the first ion selective electrode 2, with a reference element 18, a reference electrolyte 19 and an electrochemical liquid junction 20 arranged in the housing wall. Reference element 18 is electrically connected with the measurement circuit 15 of the second ion selective electrode 3. Measurement circuit 15 is embodied like the measurement circuit 8 of the first ion selective electrode 2 to register a potential difference between the reference element 18 and the potential sensing element 17 and to output such, or a signal derived therefrom, as a measurement signal of the second ion selective electrode 3 to the superordinated control unit 12 connected with the measurement circuit 15.

Control unit 12 includes an electronic data processing system and can be embodied, for example, as a measurement transmitter or as a conventional computer, as a tablet PC, as a mobile telephone, as a handheld or as a communication circuit connected via a fieldbus or via a conductor loop with a process control station. The connection between the control unit 12 and the measuring circuits 8, 15 can accordingly be embodied wired or wirelessly. The data processing system of the control unit 12 includes a computer system having at least one processor and a data memory, which the processor can access for performing computer programs stored in the data memory. Stored in the data memory is a computer program, which serves for registering the measurement signals provided by the first ion selective electrode 2 and the second ion selective electrode 3 and for determining orthophosphate content of the liquid 6 based on these measurement signals according to the method explained in greater detail below.

Figure 3:
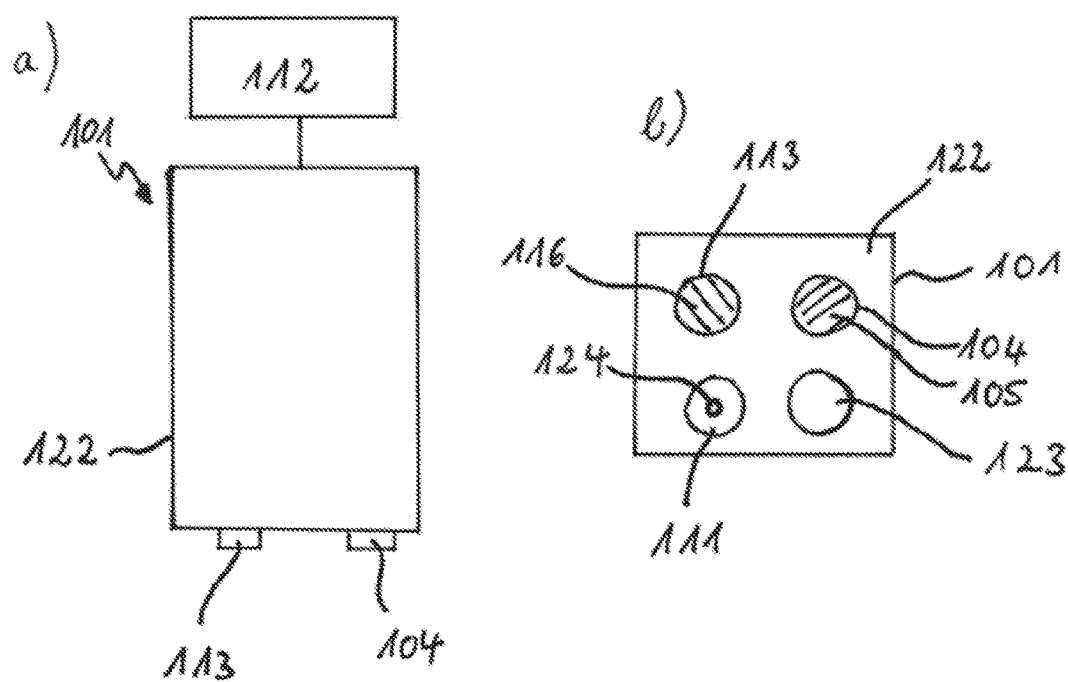
FIG. 3 is a schematic representation of a second sensor arrangement for determining orthophosphate content.

FIG. 3 shows schematically a second example of an embodiment of a sensor arrangement 101 for determining the orthophosphate content of a liquid, wherein FIG. 3a) shows the sensor arrangement 101 in a side view and FIG. 3b) the sensor arrangement 101 from below.

Sensor arrangement 101 includes a housing 122, in which a first measuring half cell 104, a second measuring half cell 113 and a reference half-cell 111 are arranged. The first measuring half cell 104 includes an ion selective membrane 105, at which in contact with a liquid a potential arises dependent on the DHP concentration in the liquid. The second measuring half cell 113 includes an ion selective membrane 116, at which in contact with the liquid a potential arises dependent on the MHP concentration in the liquid. It should be pointed out that the measuring half cells 104, 113 can be embodied, in each case, identically to the measuring half cells 4, 13 of the first example of an embodiment illustrated based on FIG. 2. Among other things, they comprise the potential sensing elements in electrical contact with a measurement circuit accommodated in the housing 122. The reference half-cell 111 includes an electrochemical liquid junction 124, via which a reference electrolyte contained in the reference half-cell is in contact in measurement operation of the sensor arrangement 101 with water to be measured. Arranged in the reference half-cell is, moreover, a reference element in contact with the reference electrolyte and embodiable essentially equally to the reference element of the reference half-cells 9, 19 in the first example of an embodiment. The reference element is electrically connected with the measurement circuit accommodated in the housing 122.

In the example of an embodiment shown here, the measurement circuit is embodied to produce a first measurement signal based on a potential difference registrable between the potential sensing element of the first measuring half cell 104 and the reference element of the reference half-cell 111 and a second measurement signal based on a potential difference registrable between the potential sensing element of the second measuring half cell 113 and the reference element of the reference half-cell 111 and to forward such to the control unit 112. Thus, with the two measuring half cells 104, 113 and the reference half-cell 111, two potentiometric, ion selective electrodes are formed, which utilize a shared reference half-cell.

Control unit 112 can be embodied equally to the control unit 12 described in the first example of an embodiment (FIG. 2).

Arranged in the housing is a further sensor 123, which can be embodied e.g. as a redox sensor or as a pH sensor, for registering additional measured variables. If such is a pH sensor, its measured value can serve to check the validity or quality of the approximation used for determining orthophosphate concentration with the sensor arrangement 101, wherein the orthophosphate content is determined essentially by the concentrations of DHP and MHP at the currently present pH-value.

Figure 4:
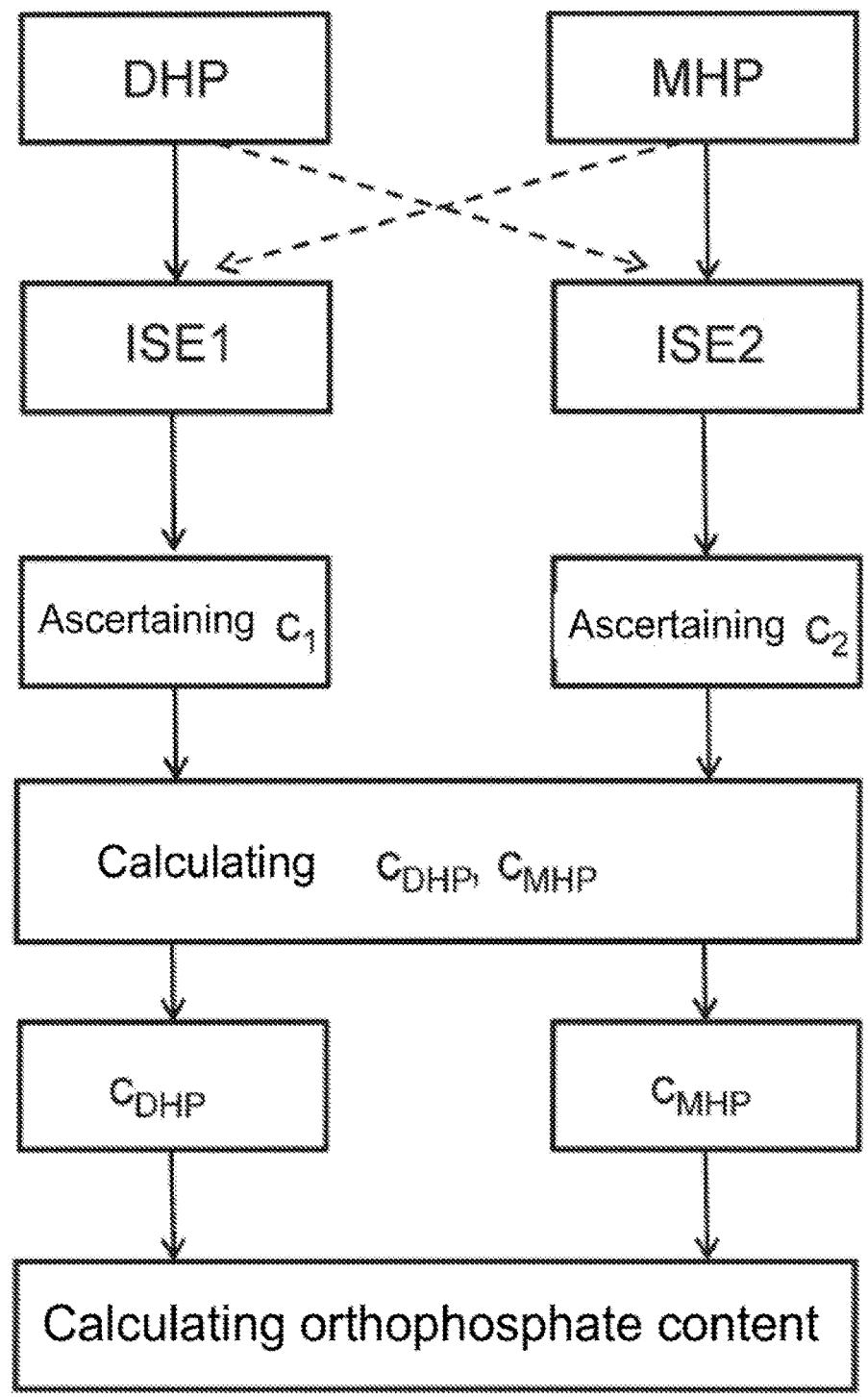
FIG. 4 is a flow diagram for conducting a method for determining orthophosphate content by means of the first or second sensor arrangement.

Based on the flowchart illustrated in FIG. 4, a method executable automatically by means of the computer program stored in the data memory of the control unit 12, respectively 112, for determining the orthophosphate content of a liquid 6 will now be described.

The ion selective DHP electrode 2 provides a first measurement signal ISE1, which depends essentially on the DHP concentration of the liquid 6. The ion selective MHP electrode 3 provides a second measurement signal ISE2, which depends essentially on the MHP concentration of the liquid 6. Based on association specifications furnished in a memory of the measuring circuits and/or the control unit 12, 112, for example, in the form of calibration functions ascertained by calibration measurements, there can be ascertained from the first measurement signal ISE1 a DHP concentration $c_1$ and from the second measurement signal ISE2 a MHP concentration $c_2$.

Ion selective electrodes respond selectively, however, not specifically, to certain ions. The first, ion selective, DHP electrode 2 responds, for example, also to MHP (indicated by the dashed arrow in FIG. 4). On the other hand, the second, ion selective, MHP electrode 3 responds also to DHP (indicated by the dashed arrow in FIG. 4). The effect of these cross sensitivities to the MHP, respectively DHP, concentrations ascertained based on the measurement signals ISE1 and ISE2 is expressed by the Nikolsky-Eisenman equations:

$$c_1 = c_{DHP} + (k_1 c_{MHP})^{1/2} \quad (1)$$

and $$c_2 = c_{MHP} + (k_2 c_{DHP})^2 \quad (2),$$

wherein $k_1$ is the selectivity coefficient of the ion selective DHP electrode, $k_2$ is the selectivity coefficient of the ion selective MHP electrode, $c_{DHP}$ is a corrected DHP concentration cleaned of the cross-sensitivity relative to MHP and $c_{MHP}$ is a corrected MHP concentration cleaned of the cross-sensitivity relative to DHP. Evident from equations (1) and (2) is that a simple summing of the concentrations $c_1$ and $c_2$ ascertained from the measurement signals ISE1, ISE2 would lead to a somewhat too high orthophosphate content.

In an additional method step, consequently, from $c_1$ and $c_2$ with application of the known selectivity coefficients $k_1$, $k_2$, the corrected concentrations $c_{DHP}$ and $c_{MHP}$ are ascertained. For this, the system of equations formed of equations (1) and (2) is utilized. Thus, there results, for example, for the corrected DHP concentration, after simplifying the expression, $$c_{DHP} = \frac{c_1 - \sqrt{k_1(k_1 k_2^2 + 1)c_2 - k_1 k_2^2 c_1^2}}{k_1 k_2^2 + 1}$$

From the so ascertained, corrected DHP concentration, with the assistance of equation (2), the corrected MHP concentration can be calculated as follows:

$$c_{MHP} = c_2 - (k_2 c_{DHP})^2.$$

By adding the so ascertained, corrected, DHP and MHP concentrations, then the orthophosphate content of the liquid can be determined.

Alternatively, from the system of equations formed from equations (1) and (2), the corrected MHP concentration can, first of all, be calculated according to the expression $$c_{MHP} = c_2 - k_2^2 \left( \frac{c_1 - \sqrt{k_1(k_1 k_2^2 + 1)c_2 - k_1 k_2^2 c_1^2}}{k_1 k_2^2 + 1} \right)^2$$

and from the so ascertained, corrected MHP concentration with the assistance of equation (1), the corrected DHP concentration is then calculated as follows:

$$c_{DHP} = c_1 - (k_1 c_{DHP})^{1/2}.$$

Clear to the skilled in the art is that correspondingly simplified or approximated forms of the here mentioned equations can be used for the corrected MHP and DHP concentrations, without deviating from the concepts of the invention.

The orthophosphate content results equally as in the case of the above described variant by adding the corrected concentrations.

The invention claimed is:

1. A method for determining the orthophosphate content of a liquid, comprising the steps of:
   contacting the liquid with an ion selective dihydrogen phosphate sensor, including an ion selective dihydrogen phosphate electrode, which thereupon generates a first measurement signal;
   contacting the liquid with an ion selective hydrogen phosphate sensor, including an ion selective hydrogen phosphate electrode, which thereupon generates a second measurement signal;
   registering the first measurement signal to an electronic control unit configured to receive and to digitize measurement signals generated by ion selective sensors;

registering the second measurement signal to the control unit; and determining the orthophosphate content of the liquid based on the first and the second measurement signals using the control unit, wherein:

a dihydrogen phosphate concentration is determined from the first measurement signal, and a hydrogen phosphate concentration is determined from the second measurement signal;

the dihydrogen phosphate concentration determined from the first measurement signal and the hydrogen phosphate concentration determined from the second measurement signal are corrected by determining a corrected dihydrogen phosphate concentration using a cross-sensitivity of the dihydrogen phosphate electrode to hydrogen phosphate present in the liquid and by determining a corrected hydrogen phosphate concentration using a cross-sensitivity of the hydrogen phosphate electrode to dihydrogen phosphate present in the liquid; and the corrected dihydrogen phosphate concentration and the corrected hydrogen phosphate concentration are determined from the concentrations determined based on the measurement signals with application of selectivity coefficients of the dihydrogen phosphate electrode and the hydrogen phosphate electrode, based on a system of equations comprising:

$$c_1 = c_{DHP} + (k_1 c_{MHP})^{1/2}$$

and $$c_2 = c_{MHP} + (k_2 c_{DHP})^2,$$

wherein $c_1$ is the dihydrogen phosphate concentration determined from the first measurement signal, $c_2$ is the hydrogen phosphate concentration determined from the second measurement signal, $k_1$ is the selectivity coefficient of the dihydrogen phosphate electrode, and $k_2$ is the selectivity coefficient of the hydrogen phosphate electrode.

2. The method as claimed in claim 1, wherein:
the corrected dihydrogen phosphate concentration is ascertained based on the equation:

$$c_{DHP} = \frac{c_1 - \sqrt{k_1(k_1 k_2^2 + 1)c_2 - k_1 k_2^2 c_1^2}}{k_1 k_2^2 + 1},$$

wherein $c_1$ is the dihydrogen phosphate concentration ascertained from said first measurement signal, $c_2$ is the hydrogen phosphate concentration ascertained from said second measurement signal, $k_1$ is the selectivity coefficient of the dihydrogen phosphate electrode, and $k_2$ is the selectivity coefficient of the hydrogen phosphate electrode; and based on the corrected dihydrogen phosphate concentration, a corrected hydrogen phosphate concentration is calculated based on the equation:

$$c_{MHP} = c_2 - (k_2 c_{DHP})^2.$$

3. The method as claimed in claim 1, wherein:
the corrected hydrogen phosphate concentration is ascertained based on the equation:

$$c_{MHP} = c_2 - k_2^2 \left( \frac{c_1 - \sqrt{k_1(k_1 k_2^2 + 1)c_2 - k_1 k_2^2 c_1^2}}{k_1 k_2^2 + 1} \right)^2,$$

wherein $c_1$ is the dihydrogen phosphate concentration ascertained from said first measurement signal, $c_2$ is the hydrogen phosphate concentration ascertained from said second measurement signal, $k_1$ is the selectivity coefficient of the dihydrogen phosphate electrode, and $k_2$ is the selectivity coefficient of the hydrogen phosphate electrode; and based on the corrected hydrogen phosphate concentration, a corrected dihydrogen phosphate concentration is calculated based on the equation:

$$c_{DHP} = c_1 - (k_1 c_{DHP})^{1/2}.$$

4. The method as claimed in claim 1, wherein:
the orthophosphate concentration is determined by adding the corrected dihydrogen phosphate concentration and the corrected hydrogen phosphate concentration.

5. The method as claimed in claim 1, wherein:
the liquid is an aqueous liquid.

6. The method as claimed in claim 1, wherein:
the liquid has a pH-value between 5 and 10.

7. The method as claimed in claim 1, wherein:
the liquid is waste water treated in an industrial or municipal clarification plant.

8. A method for determining the orthophosphate content of a liquid, comprising the steps of:

contacting the liquid with an ion selective dihydrogen phosphate sensor, including an ion selective dihydrogen phosphate electrode, which thereupon generates a first measurement signal;

contacting the liquid with an ion selective hydrogen phosphate sensor, including an ion selective hydrogen phosphate electrode, which thereupon generates a second measurement signal;

registering the first measurement signal to an electronic control unit configured to receive and to digitize measurement signals generated by ion selective sensors;

registering the second measurement signal to the control unit;

determining a dihydrogen phosphate concentration and a hydrogen phosphate concentration from the first and second measurement signals, respectively;

correcting the dihydrogen phosphate concentration for a cross-sensitivity of the dihydrogen phosphate electrode to hydrogen phosphate and thereby ascertaining a corrected dihydrogen phosphate concentration using the control unit;

correcting the hydrogen phosphate concentration for a cross-sensitivity of the hydrogen phosphate electrode to dihydrogen phosphate and thereby ascertaining a corrected hydrogen phosphate concentration using the control unit; and ascertaining the orthophosphate content of the liquid as a sum of the corrected dihydrogen phosphate concentration and the corrected hydrogen phosphate concentration using the control unit, wherein:

the corrected dihydrogen phosphate concentration and the corrected hydrogen phosphate concentration are determined from the concentrations determined based on the measurement signals with application of selectivity coefficients of the dihydrogen phosphate electrode and the hydrogen phosphate electrode, based on a system of equations comprising:

$$c_1 = c_{DHP} + (k_1 c_{MHP})^{1/2}$$

and $$c_2 = c_{MHP} + (k_2 c_{DHP})^2,$$

wherein $c_1$ is the dihydrogen phosphate concentration determined from the first measurement signal, $c_2$ is the hydrogen phosphate concentration determined from the second measurement signal, $k_1$ is the selectivity coefficient of the dihydrogen phosphate electrode, and $k_2$ is the selectivity coefficient of the hydrogen phosphate electrode.

9. The method as claimed in claim 8, wherein:
the liquid is waste water treated in an industrial or municipal clarification plant.

10. A method of monitoring or controlling phosphate elimination from water, phosphate reclamation from water, or water treatment in a clarification plant, comprising:
contacting the water with an ion selective dihydrogen phosphate sensor, including an ion selective dihydrogen phosphate electrode, which thereupon generates a first measurement signal;
contacting the water with an ion selective hydrogen phosphate sensor, including an ion selective hydrogen phosphate electrode, which thereupon generates a second measurement signal;
registering the first measurement signal to an electronic control unit configured to receive and to digitize measurement signals generated by ion selective sensors;
registering the second measurement signal to the control unit;
determining a dihydrogen phosphate concentration and a hydrogen phosphate concentration from the first and second measurement signals, respectively;
correcting the dihydrogen phosphate concentration for a cross-sensitivity of the dihydrogen phosphate electrode to hydrogen phosphate and ascertaining a corrected dihydrogen phosphate concentration using the control unit;
correcting the hydrogen phosphate concentration for a cross-sensitivity of the hydrogen phosphate electrode to dihydrogen phosphate and ascertaining a corrected hydrogen phosphate concentration using the control unit;
determining the orthophosphate content of the water based on the corrected dihydrogen phosphate concentration and on the corrected hydrogen phosphate concentration using the control unit; and
controlling the phosphate elimination, phosphate reclamation or water treatment in the clarification plant based on the determined orthophosphate content.

\* \* \* \* \*